United States Patent [19]

Holtkamp, Sr.

[11] Patent Number: Plant 7,088

[45] Date of Patent: Dec. 26, 1989

[54] AFRICAN VIOLET PLANT NAMED DÉCENNIE

[76] Inventor: Reinhold Holtkamp, Sr., Werther Strasse 112, D4294 Isselburg, Fed. Rep. of Germany

[21] Appl. No.: 251,322

[22] Filed: Sep. 30, 1988

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Décennie which is a sport of Gisela, disclosed in U.S. Plant patent application Ser. No. 056,388. Décennie is characterized its single, dark purplish pink flowers with wavy, frilled edges; strong, upright flower stems that curve slightly toward the center to form a tight bouquet above the leaves; medium green, slightly serrated leaves, profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha*, and hereinafter referred to by the cultivar named Décennie.

The new cultivar was referred to during the breeding and selection process by the designation M/I 11/16, and is a sport of Gisela, disclosed in my pending U.S. Plant patent application Ser. No. 056,388. Décennie is similar in all essential respects to Gisela except for its dark purplish pink flower color.

Décennie was discovered in a flowering block of the parent cultivar Gisela, and subsequently selected. Asexual reproduction of the new cultivar by leaf cutting, as performed by me at Haffen, West Germany, has demonstrated that the combination of characteristics as herein disclosed for the new cultivar are firmly fixed and retained through successive generations of asexual reproduction.

Décennie has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Décennie, which in combination distinguish this African violet as a new and distinct cultivar:

(1) Strong, upright flower stems curving slightly toward the center.

(2) Violet-shaped, dark purplish pink flowers with lighter pink wavy, frilled edges.

(3) Profuse flowering.

(4) Each plant carries 8–10 and more upright flower stems, each of which carries 5–8 and more flowers.

(5) Long lasting, non-dropping flowers.

(6) Vigorous grower.

(7) First flash of flowers appears 9–10 weeks after potting and forms a tight bouquet above the leaves.

(8) Plant saleable 10 to 11 weeks after potting.

(9) Seed capsules push slightly through.

(10) Medium green, round to heart-shaped leaves.

(11) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 1 p.m. in Nashville, Tenn.

Botanical Classification: *Saintpaulia ionantha,* Ramat., c.v. Décennie.

Parentage: Sport of Gisela, disclosed in U.S. Plant patent application Ser. No. 056,388.

Propagation: The new cultivar holds its distinguishing characteristics through successive propagations by leaf cuttings.

Plant: From 9 cm to 11 cm tall when grown in pots, and approximately 23–26 cm in diameter when fully grown.

*Leaves.*—General form: Round or heart-shaped. Diameter: 60–75 mm. Texture: Velvety. Aspect: Shiny, hairy. Veins: Upperside: visible; underside: well pronounced, light green and shiny; purplish in between the veins. Color (upperside): Yellow-Green Group 147 between A and B. Color (underside): Greyed-Green Group 194 between C and D. Petiole: Strong upright, light green with purplish brown touch, hairy.

*Flowers.*—Buds: Bell-shaped, 7–8 mm just before opening, light green with purplish touch. Sepals: Five (5). Color: Green with browish touch. Calyx: Shape: Funnel-shaped. Aspect: Spear-shaped, hairy. Peduncle: Character: Strong upright, hairy. Color: Purplish brown. Individual flowers: Size: 45–50 mm. Shape: Single violet-shaped (3 large and 2 small petals) with wavy and frilled edges. Color (upperside): Purple Group 78 between A and B, in the center a touch of Red-Purple Group 59 C. The flowers appearing at the top and slightly to the right of center in the photograph very closely depict flower color.

There are a few flowers that appear more red than the stated color values, but that is due to imperfections in the photographic process. Under cooler temperature and more intensive lighting, the color tends to intensify. Color (underside): Purple Group 78 between B and C. Borne: Each flower stem carries 5–8 and more flowers on strong, upright peduncles that are free standing above the leaves, thereby forming a compact bouquet. Flowering habit: Flowers 9–10 weeks after potting.

*Reproductive organs.*—Stamens: Two (2). Anthers: 2 composed of 4 anther cells, seed capsule pushes slightly through. Filaments: Yellowish green with purplish traces 5 mm long. Pollen color: Yellow Group 7 A. Styles: 7–8 mm long, purplish red, base of ovary light green and hairy. Roots: Normally developed, white when young, turning slightly brownish when older.

Disease resistance: Good.

General observations: Décennie is a very attractive, vigorous grower with dark purplish pink flowers contrasting nicely with the bright yellow anthers. Each of the 8–10 and more flowers stems carries 5–8 and more single, violet-shaped flowers with wavy, frilled edges. The color is less intensive around the edge. The flowers are long-lasting and non-dropping and the seed capsule pushes slightly through. A tight bouquet of flowers free standing above the medium green, slightly serrated leaves develops after approximately 9–10 weeks.

I claim:

1. A new and distinct cultivar of African violet named Décennie, as described and illustrated, and particularly characterized by its single, dark purplish pink flowers with wavy, frilled edges; strong, upright flower stems that curve slightly toward the center to form a tight bouquet above the leaves; medium green, slightly serrated leaves; profuse flowering, vigorous growth habit, flowering 9–10 weeks after potting, and its long-lasting and non-dropping flowers.

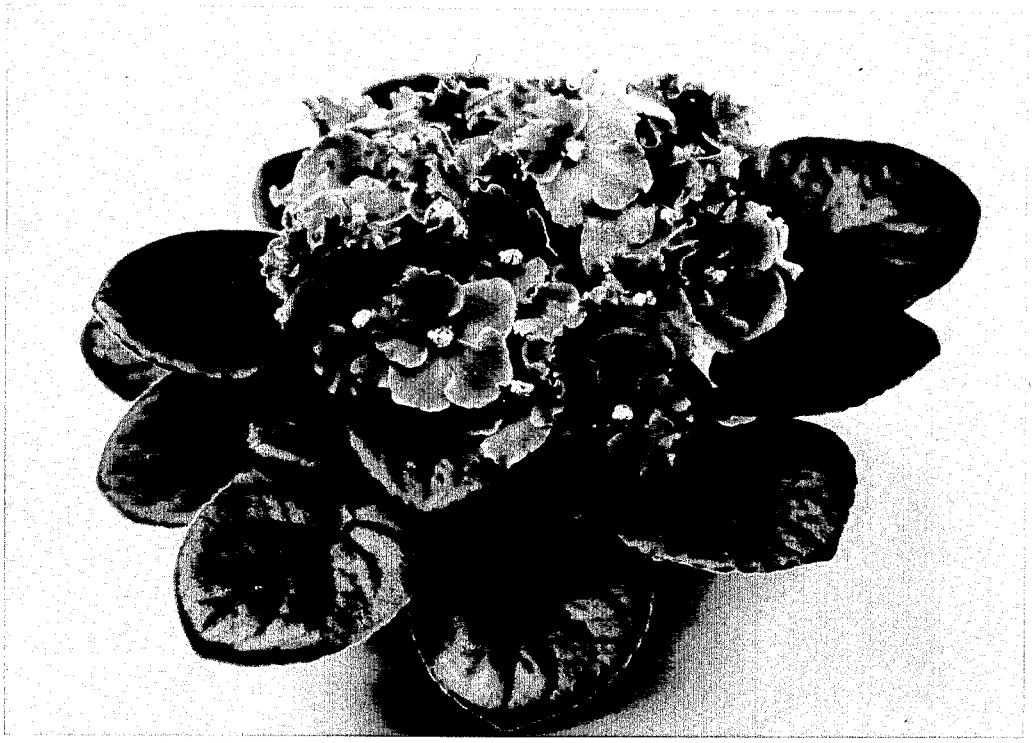

* * * * *